(12) United States Patent
Guasch

(10) Patent No.: US 8,182,762 B2
(45) Date of Patent: May 22, 2012

(54) DEVICE FOR DISTRIBUTING PARTICLES IN A FLUID AND METHODS THEREOF

(75) Inventor: Joan Francesc Guasch, Barcelona (ES)

(73) Assignee: Biokit, S.A., Barcelona (ES)

( * ) Notice: Subject to any disclaimer, the term of this patent is extended or adjusted under 35 U.S.C. 154(b) by 670 days.

(21) Appl. No.: 12/088,913

(22) PCT Filed: Jan. 14, 2008

(86) PCT No.: PCT/ES2008/000013
§ 371 (c)(1),
(2), (4) Date: Apr. 1, 2008

(87) PCT Pub. No.: WO2009/090272
PCT Pub. Date: Jul. 23, 2009

(65) Prior Publication Data
US 2010/0189604 A1    Jul. 29, 2010

(51) Int. Cl.
*G01N 33/00* (2006.01)
(52) U.S. Cl. ........ 422/402; 422/401; 422/405; 422/408; 422/500
(58) Field of Classification Search .............. 422/401, 422/402, 405, 408, 500
See application file for complete search history.

(56) References Cited

U.S. PATENT DOCUMENTS

| | | | |
|---|---|---|---|
| 3,087,707 A | 4/1963 | Moonan | |
| 3,184,118 A | 5/1965 | Webster | |
| 4,108,974 A | 8/1978 | Wegfahrt et al. | |
| 4,454,234 A | 6/1984 | Czerlinski | |
| 4,640,623 A | 2/1987 | Tornell | |
| 4,641,974 A | 2/1987 | Church | |
| 5,236,262 A | 8/1993 | Espey | |
| 5,544,960 A | 8/1996 | Sommovigo | |
| 6,875,447 B2 | 4/2005 | Bartholomaus et al. | |
| 7,364,906 B2 * | 4/2008 | Pankowsky | 436/10 |

FOREIGN PATENT DOCUMENTS

| | | |
|---|---|---|
| EP | 1729136 | 12/2006 |
| JP | 2003339375 | 12/2003 |

OTHER PUBLICATIONS

Brandl, et al., "Preparation and characterization of semi-solid phospholipid dispersions and dilutions thereof", International Journal of Pharmaceutics 170:187-199 (1998).
International Search Report for PCT/ES2008/000013 mailed Aug. 12, 2008 (4 pgs.).
Written Opinion of the International Searching Authority for PCT/ES2008/000013 mailed Aug. 12, 2008 (5 pgs.).
International Preliminary Report on Patentability for PCT/ES2008/000013 mailed Jul. 20, 2010 (6 pages).

* cited by examiner

*Primary Examiner* — Sam P Siefke
(74) *Attorney, Agent, or Firm* — Burns & Levinson LLP

(57) ABSTRACT

A vial and particles for distributing reagent bound particles in a fluid, a kit, and methods for distributing particles in a fluid.

29 Claims, 2 Drawing Sheets

DEVICE FOR DISTRIBUTING PARTICLES IN A FLUID AND METHODS THEREOF

CROSS REFERENCE TO RELATED APPLICATIONS

This application is the U.S. National Phase Application of International Patent Application Serial No. PCT/ES2008/000013, filed Jan. 14, 2008, the entire disclosure of which is incorporated by reference herein.

TECHNICAL FIELD

The invention relates to a stirring device for suspending coated particles forming the solid phase of a fluid for in vitro diagnostic assays.

BACKGROUND

Most commonly, in vitro diagnostic assays that use a liquid suspension of a solid phase support such as particles, for example, paramagnetic particles require a homogeneous suspension of such particles to be useful in the diagnostic assay. These particles tend to settle to the bottom of a container when the container holding the particles is stored in an upright, non-moving position. The particles require mixing to bring them back to liquid homogeneous suspension before the particles can be used in a diagnostic assay.

Commonly used mixers in automated clinical analyzers typically consist of rotors for generating rotary movement of the particle container or rotary movement of an element within the particle container for a given period of time before the particles in the container may be sampled for use in a diagnostic assay. Mixing to resuspend the particles during the rotary movement is commonly aided by turbulence in the container generated by frequent changes of direction of the rotary movement and by the internal design of the container itself.

Presently, known mixers used in automated clinical analyzers fail to achieve complete resuspension and homogenization of particles. A common cause for this failure arises from the difficulty in disrupting interactions formed by the coated particles. These interactions will occur more frequently when the particles have settled to the bottom of their container. Such interactions are commonly due to electrostatic and hydrophobic interactions, either between the surface of the particles or between the surface of the particles and the walls of the container. Small aggregates of particles formed due to these interactions are particularly difficult to disrupt using solely rotary movement of the container.

An improved mixing system for rapidly and thoroughly resuspending and homogenizing coated particles useful as the solid phase support component in in vitro diagnostic assays is needed.

SUMMARY OF THE INVENTION

In one aspect, the invention relates to a kit for uniform distribution of particles in a fluid. In one embodiment, the kit, according to the invention, comprises a vial. The vial is suitable for holding a fluid. The kit also includes a plurality of first particles, each of the first particles having a diameter. A reactant is bound to at least one of the first particles. The kit further includes a plurality of second particles, each of the second particles having a diameter. The ratio of the diameter of the second particles to the diameter of the first particles is in the range of about 100:1, 1000:1, or about 10,000:1.

In one embodiment of the kit, the vial comprises an opening for introducing an aspirator. In another embodiment, the vial includes an intraluminal agitator joined to the vial.

In a particular embodiment of the kit, the vial is non-pressurized, for example the contents of the vial are at atmospheric pressure.

The reactant bound to the at least one first particle may be at least one antibody, protein, or nucleic acid. In a particular embodiment, the second particles are not bound by reactants; i.e., the second particles are free of reactants. According to one embodiment of the kit according to the invention, the plurality of first and second particles are enclosed in the vial.

In another aspect, the invention relates to a cartridge for an automated clinical analyzer including a plurality of vials for holding reagents useful in a diagnostic assay. The cartridge features at least one rotatable vial and a plurality of first particles and second particles enclosed by the vial. The ratio of the diameter of the second particles to the diameter of the first particles is in the range of, for example, 10,000:1. In one embodiment, the rotatable vial has a top with an opening for probe access. The cartridge provides a reagent and a plurality of first particles for the analysis of a target analyte in a patient body fluid by the automated clinical analyzer.

In another aspect, the invention relates to a method for uniformly distributing particles in a fluid. The method includes the steps of providing a plurality of first particles, a fluid, and a vial. The vial is suitable for holding the fluid and the first particles. The method further provides a plurality of second particles, the second particles comprising a width at least ten times larger than the width of the first particles. The second particles, first particles, and the fluid are placed in the vial and the vial holding the second particles, first particles, and fluid, is rotated whereby the first particles are uniformly distributed in the fluid.

These and other objects, along with advantages and features of the present invention herein disclosed, will become apparent through references to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

The foregoing and other objects, features and advantages of the present invention disclosed herein, as well as the invention itself, will be more fully understood from the following description of preferred embodiments and claims when read together with the accompanying drawings. The drawings are not necessarily to scale, emphasis instead generally being placed upon illustrating the principles of the invention.

DESCRIPTION

In one aspect, the invention is a system for mixing first particles in a fluid. The first particles 10 are typically round, or substantially round. Typically, the fluid is a buffer or a fluid reagent. The first particles 10 have a reactant bound to the particle surface. The first particles 10 provide a solid support for the reactants in an in vitro assay for a target analyte, for example a target antibody or a target antigen, in a patient's body fluid. The patient's body fluid may be whole blood, serum, plasma, synovial fluid, cerebro-spinal fluid, or urine, for example.

In one aspect, the invention relates to a kit for mixing first particles 10 in a fluid. The kit includes a vial 20, a plurality of first particles 10, and a plurality of second particles 12. The kit further includes a reactant associated with, for example, bound to, at least one of the plurality of first particles 10. As used herein a reactant means a substance that interacts with an analyte in a patient's body fluid. The second particles 12 each have a diameter that is larger than the diameter of the first particles 10 and may be similar or different in composition than the first particles 10. Typically, a reactant is not associated with the second particles 12.

Figure 1:
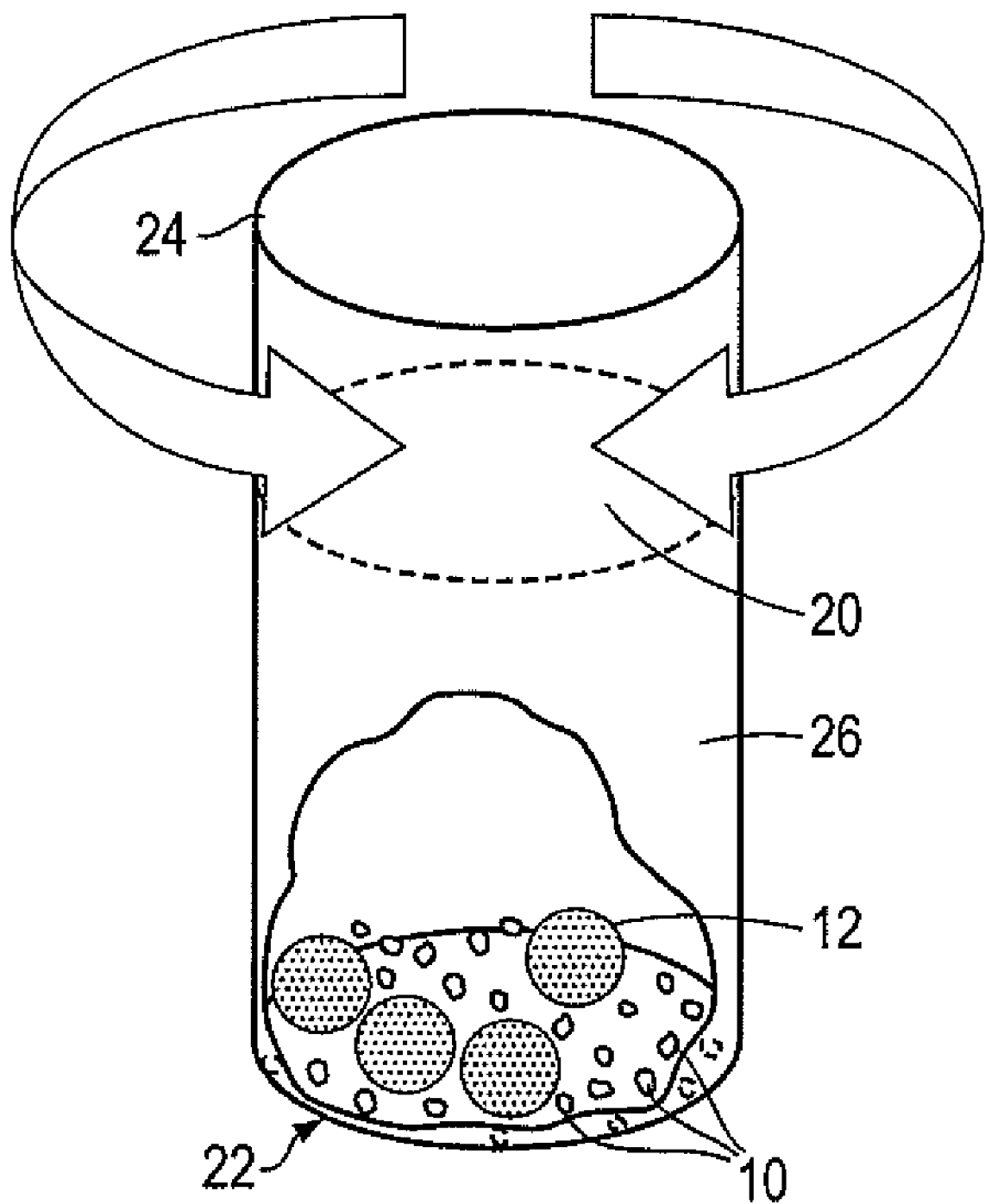
FIG. 1 illustrates a vial enclosing first particles and second particles according to one embodiment of the invention.

Referring to FIG. 1, in one embodiment of the kit according to the invention, the vial 20 is substantially cylindrical, and has a bottom 22 to form a compartment capable of holding a fluid. The bottom 22 of the vial 20 may be flat, concave, or convex. In one embodiment of the invention, the top 24 of the vial 20 has an opening or a perforable seal suitable for introducing a probe such as, for example, an aspirator probe or an agitator probe. In another embodiment of the invention, the top 24 of the vial 20 includes a cap (not illustrated), for example, a removable cap. In a particular embodiment, the vial 20 is non-pressurized. For example, the vial contents are maintained at atmospheric pressure before, during, and after agitation of the first particles in the vial.

In another embodiment, the vial 20 includes an intraluminal agitator (not shown). The intraluminal agitator may be, for example, a longitudinal projection that projects from the wall of the vial 20 into the lumen 26 of the vial 20. The intraluminal agitator may extend from the top 24 of the vial 20 to the bottom 22 of the vial 20 or along any vertical length of the cylinder of the vial 20.

In one embodiment of the kit according to the invention, the first particles 10 are made from materials such as polymers, for example latex or polystyrene, acrylics, polycarbonate, polyethylene, polypropylene, glass, paramagnetic materials, metal such as stainless steel, titanium, nickel titanium and metal alloys, ceramics, or combinations of the above. The width or the diameter of each of the first particles 10 is, for example, in the range of about 0.01 micrometers to 7 micrometers, preferably 0.2 micrometers to 6 micrometers, more preferably 0.3 micrometers to 5 micrometers, 5 micrometers, or 1 micrometer.

Reactants bound to the first particles 10 are, for example, one or more antibodies, antigens, analytes, receptors or its ligand, lectins, proteins, nucleic acids, lipids, polymers, fragments of the above, or combinations of the above. In particular examples, the reactant bound to the first particle 10 is beta$_2$ glycoprotein, cardiolipin-beta-2-glycoprotein I complex, PVS-PF4 complex, monoclonal antibody, polyclonal antibody, or a viral antigen.

The second particles 12, according to the invention, are made from materials such as polymers, for example latex or polystyrene, acrylics, polycarbonate, polyethylene, polypropylene, glass, paramagnetic materials, metals such as stainless steel, titanium, nickel-titanium and metal alloys, ceramics, or combinations of the above. The materials used to make the second particles 12 are inert and will not interfere with or be damaged by components of the reagents or sample fluid placed in the vial. The second particles 12 are large enough and of sufficient mass that they do not remain in suspension in a fluid after agitation. The width or diameter of the second particles 12 is larger than the width or diameter of the first particles 10. For example, the ratio of the diameter of the second particles 12 to the diameter of the first particles 10 is in the range of about 10:1 to 100:1, 100:1 to 1000:1, 1000:1 to 10,000:1, or 10,000:1 to 100,000:1. Preferably, the ratio is in the range of 1000:1, more preferably 3000:1. The diameter of the second particles 12 may be in the range of about 100 micrometers to 10 millimeters, preferably 1 millimeter to 8 millimeters, more preferably 2 millimeters to 6 millimeters, more preferably 3 millimeters to 4 millimeters.

In one embodiment of the kit, the first particles 10 and the second particles 12 are packaged together in the vial 20. Alternatively, only the first particles 10 are packaged in the vial 20. In this embodiment, the second particles 12 are included but separately packaged in the kit from the first particles 10. In yet another embodiment, each of the vial 20, first particles 10, and second particles 12 of the kit are packaged separately in the kit.

According to the invention, when placed in the vial 20 the second particles 12 cover from about 5% to 75%, preferably 10 to 50%, more preferably 25-50% of the surface of the bottom 22 of the vial 20. For example, in one embodiment four second particles 12 each having a diameter of about 3 mm are placed in a vial 20 having a bottom diameter of about 15 mm. Alternatively, for example, 6-8 second particles 12 each having a diameter of about 3 mm are placed in a vial 20 having a bottom diameter of about 30 mm. The percentage of the surface of the bottom 22 of the vial 20 that is covered and is within these ranges enhances suspension of the first particles 10 when the vial 20 holding the first particles 10 and the second particles 12 is rotated, preferably rotated in an oscillating, i.e., to-and-fro pattern. According to the invention, rotation of the vial 20 provides superior homogeneous and/or more rapid mixing of the first particles 10 in the presence of the second particles 12 than rotation of the vial 20 with the first particles 10 alone.

According to one embodiment of the invention, the first particles 10 suspended in the presence of the second particles 12 remain in suspension in the range of about, for example, 1 second to 120 minutes, 20 seconds to 240 seconds, or 5 seconds to 60 seconds after rotation has stopped.

According to the invention, the kit may further include a cartridge (not shown). The cartridge may be suitable for insertion in an automated clinical analyzer. In one embodiment of the invention, the cartridge includes at least one rotatable vial 20 enclosing a plurality of first particles 10, e.g., paramagnetic particles and at least one second particle 12. The rotatable vial 20 may house a fluid such as a buffer. In one embodiment, the cartridge may include one or more non-rotatable vials. Each of the one or more non-rotatable vials may house one or more reagents to be used in the assay.

The analyzer may include a probe (not shown), e.g., an aspirator, for insertion through the top of the vial 20 holding the first particles 10 to aspirate and transfer the first particles 10 to a reaction chamber such as a cuvette. In one embodiment of the invention, the diameter of the lumen of the probe tip that comes in contact with the fluid in the vial 20 holding the first particles 10 and second particles 12 is greater than the diameter of the first particles 10 and smaller than the diameter of the second particles 12. Alternatively, the diameter of the lumen of the probe tip is the same as or greater than the diameter of the second particles 12.

In another aspect, the invention relates to a method for mixing particles in a fluid. According to the method, the first particles 10 including a reactant bound to at least one of the first particles 10, the second particles 12, and a fluid, for example, a buffer, are placed in a vial 20. The vial 20 is placed on a rotator such as a rotating plate or a rotating rod on a clinical analytical instrument manufactured by, for example, Instrumentation Laboratory Company, Lexington, Mass. The vial 20 including the first particles 10 and the second particles 12 is rotated. According to one embodiment, rotation of the vial 20 occurs in a to and fro manner (oscillating).

During rotation of the vial 20 containing the first particles 10 and second particles 12, the second particles 12 roll along the bottom 22 of the vial 20 displacing any first particles 10 also on the bottom 22 thereby suspending the first particles 10 in the fluid in the vial 20.

Collision of the second particles 12 with aggregates of the first particles 10 aids in breaking apart aggregates of first particles 10.

EXEMPLIFICATION OF THE INVENTION

A chemiluminescent immunoassay study was conducted using a protein reagent bound to paramagnetic particles approximately 1.0 micrometer in diameter as the solid phase of the assay. Paramagnetic particles (first particles) with the bound protein were placed in two vials. In the first vial, four glass balls (second particles) each about 3 mm in diameter were added to the vial with the first particles. In the second vial, no glass balls (second particles) were added to the vial with the first particles.

The first vial and the second vial were stored for 18 hours in an upright position. After this time period, each vial was placed on the rotator of an immunoanalyzer. Resuspension of the first particles in each assay was determined after a predetermined number of rotations (oscillation) of the first and second vials. Percent resuspension is calculated as a function of the obtained assay result versus the expected result when the particles are completely resuspended.

Figure 2:
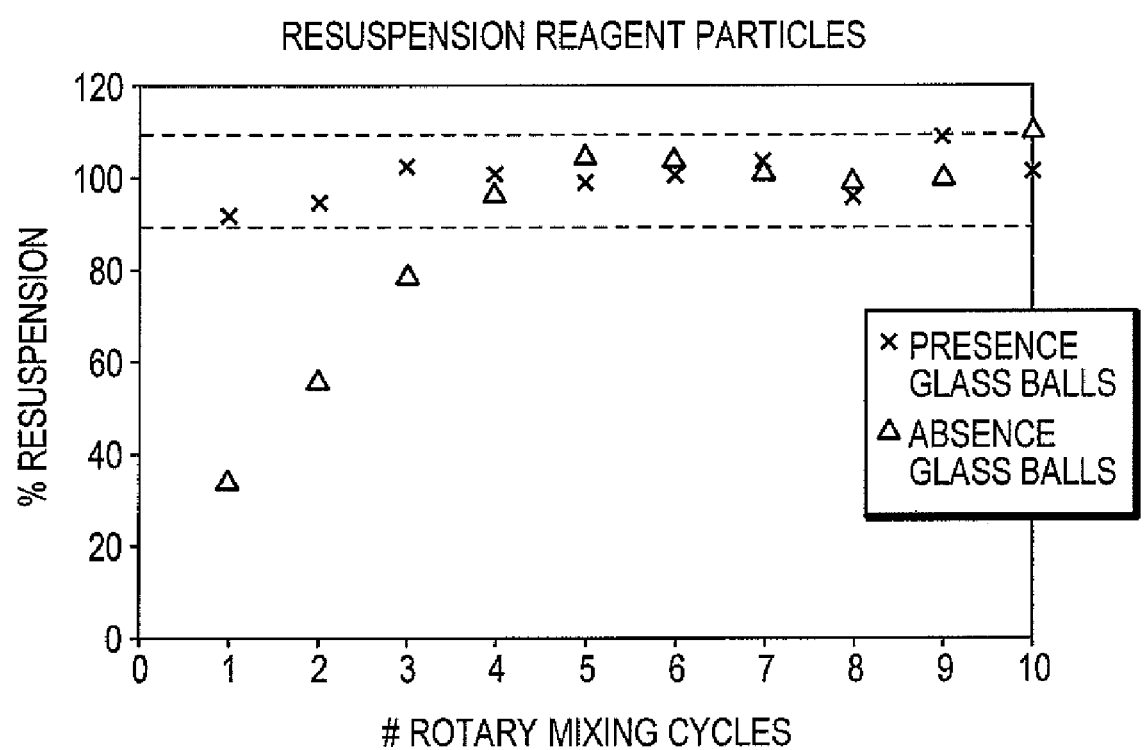
FIG. 2 is a graph of the data obtained from a chemiluminescent study of the effect of paramagnetic particle mixing in the presence and in the absence of second particles.

Referring to FIG. 2, the graph shows that in the presence of the glass balls (first vial with second particles) 100%+/−10% of expected signal is achieved after one mixing cycle. In the absence of the glass balls (second vial without second particles) only 34% of the expected signal is recovered after one mixing cycle. Only after four mixing cycles of the second vial, nearly 100% of the expected signal is obtained. From this data it is evident that the presence of the second particles enhances the suspension of the first particles in a shorter period of time than suspension of the first particles in the absence of the second particles.

What is claimed is:

1. A kit, comprising:
   a vial, said vial suitable for holding a fluid and comprising a top;
   a plurality of non-reactive, polymeric first particles enclosed in said vial, said first particles comprising a diameter;
   a reactant bound to at least one of said first particles;
   a plurality of second particles enclosed in said vial, said second particles free of reactants and comprising an inert material, and a diameter, the ratio of the diameter of the second particles to the diameter of the first particles being in the range of about 10:1 to 100:1, 100:1 to 1000:1, 1000:1 to 10,000:1, or about 10:000:1 to 100,000:1.

2. The kit of claim 1 wherein said vial further comprises an opening for introducing an aspirator.

3. The kit of claim 1 wherein said vial further comprises an intraluminal agitator joined to said vial.

4. The kit of claim 1 wherein said vial is non-pressurized.

5. The kit of claim 1 wherein said reactant comprises at least one antibody.

6. The kit of claim 1 wherein said reactant comprises at least one protein.

7. The kit of claim 1 wherein said reactant comprises at least one nucleic acid.

8. The kit of claim 1 wherein said plurality of second particles cover 5% to 75% of the surface of the bottom of said vial.

9. The kit of claim 1 wherein said plurality of second particles cover 25% to 50% of the surface of the bottom of said vial.

10. The kit of claim 3 wherein said plurality of first particles and said plurality of second particles are located intraluminally with said agitator.

11. A cartridge for an automated clinical analyzer, comprising:
    a plurality of vials comprising a lumen for holding reagents, one of said vials rotatable; and,
    a plurality of non-reactive, polymeric first particles, a reactant bound to at least one of said first particles, and a plurality of second particles free of reactants and comprising an inert material wherein the ratio of the diameter of said second particles to the diameter of said first particles is in the range of more than 1000:1 to about 10,000:1, or about 10,000:1 to 100,000:1, said first particles and second particles enclosed in said rotatable vial, said rotatable vial further comprising a top, said lumen accessible by a probe via said top wherein said cartridge provides a reagent and a plurality of first particles for the analysis by the automated clinical analyzer of a target analyte in a patient body fluid.

12. A method for uniformly suspending stored, reactant-bound, polymeric particles in a fluid, comprising:
    providing a kit comprising a plurality of non-reactive, polymeric first particles, a plurality of second particles, said second particles free of reactants and comprising an inert material and being larger than said first particles, a reactant bound to at least one of said first particles,
    a fluid,
    a vial, said vial comprising a top and holding said fluid, said first particles, and said second particles; and,
    rotating said vial holding said second particles, first particles, and fluid, whereby said first particles are uniformly suspended in said fluid.

13. The method of claim 12 wherein the ratio of the diameter of said second particles to the diameter of said first particles is in the range of about 10,000:1 to 100,000:1.

14. The method of claim 12 wherein said second particles comprise a polymer.

15. The method of claim 12 wherein said second particles comprise a ceramic material.

16. The method of claim 12 wherein said second particles comprise a metal.

17. The method of claim 12 wherein said second particles comprise a glass.

18. The method of claim 12 wherein said first particles comprise latex.

19. The method of claim 12 wherein said first particles remain substantially uniformly distributed in said fluid for a length of time in the range of about 5 seconds to 120 minutes after said rotation has stopped.

20. The method of claim 12 wherein said first particles remain substantially uniformly distributed in said fluid for a length of time in the range of about 20 seconds to 240 seconds after said rotation has stopped.

21. The method of claim 12 wherein said first particles remain substantially uniformly distributed in said fluid for a length of time in the range of about 5 seconds to 60 seconds after said rotation has stopped.

22. The method of claim 12 wherein said rotation is oscillating.

23. The method of claim 12 wherein said vial is non-pressurized.

24. The kit of claim 1 wherein said plurality of second particles cover 10% to 50% of the surface of the bottom of said vial.

25. The cartridge of claim 11 wherein said plurality of second particles cover 10 to 50% of the surface of the bottom of said vial.

26. The cartridge of claim 11 wherein said plurality of second particles cover 25 to 50% of the surface of the bottom of said vial.

27. The method of claim 12 wherein said plurality of second particles cover 10% to 50% of the surface of the bottom of said vial.

28. The method of claim 12 wherein said plurality of second particles cover 25% to 50% of the surface of the bottom of said vial.

29. The kit of claim 1 wherein the ratio of the diameter of the second particles to the diameter of the first particles is in the range of more than about 1000:1 to 10,000:1, or about 10,000:1 to 100,000:1.

* * * * *